United States Patent [19]

Kunugiza et al.

[11] Patent Number: 4,766,208

[45] Date of Patent: Aug. 23, 1988

[54] METHOD OF PERFORMING AN OXIDATION REACTION

[75] Inventors: Kiyomitsu Kunugiza; Kozo Kamiya, both of Hikari, Japan

[73] Assignee: Takeda Chemical Industries, Ltd., Osaka, Japan

[21] Appl. No.: 883,695

[22] Filed: Jul. 8, 1986

[30] Foreign Application Priority Data

Jul. 15, 1985 [JP] Japan ................... 60-156821

[51] Int. Cl.$^4$ ...................... C07B 41/00; C07B 45/00; C07H 15/16; C07H 15/20

[52] U.S. Cl. .................... 536/18.5; 536/18.6; 549/361; 562/538

[58] Field of Search ............... 536/18.5, 18.6; 562/538; 549/361

[56] References Cited

U.S. PATENT DOCUMENTS 3,451,993 6/1969 Goshima et al. ............ 549/361
4,510,306 4/1985 Langdon ..................... 536/18.6
4,618,709 10/1986 Sada et al. .................. 562/538

FOREIGN PATENT DOCUMENTS 2167416 5/1986 United Kingdom ........... 562/538

Primary Examiner—Ronald W. Griffin
Attorney, Agent, or Firm—Wenderoth, Lind & Ponack

[57] ABSTRACT

A method of performing an oxidation reaction in which an alkali hypohalite is used as an oxidizing agent which comprises: carrying out the oxidation reaction in an aqueous medium with concurrently distilling off a solvent used in the reaction as the reaction proceeds under a reduced pressure.

The method is in particular useful for the oxidation of diacetone-L-sorbose to diacetone-2-keto-L-gulonic acid in water. The reaction temperature is so accurately controlled that the same optimum yield of diacetone-2-keto-L-gulonic acid is obtained by the use of a reduced amount of sodium hypochlorite as compared with the conventional manner of reaction under atmospheric pressure.

5 Claims, No Drawings

METHOD OF PERFORMING AN OXIDATION REACTION

This invention relates to a method of performing an oxidation reaction, and more particularly, to an industrially advantageous method of performing an oxidation reaction wherein an alkali hypohalite is used as an oxidizing agent.

An alkali hypohalite such as sodium hypochlorite is frequently used as an oxidizing agent in an oxidation reaction of organic compounds. Examples of such oxidation reactions include an oxidation reaction of diacetone-L-sorbose to diacetone-2-keto-L-gulonic acid which is utilized as starting material for the production of vitamin C or L-ascorbic acid as described in Gazette of Chemical Society of Japan, 64 (10), 1729 (1961). The oxidation reaction is most advantageously carried out at a temperature of about 50°–80° C. under atmospheric pressure according to the literature. Further in the reaction, the alkali hypohalite, e.g., sodium hypochlorite, is used in a large excess, usually in amounts of about 1.3 to 3 times the theoretical amount, since not only sodium hypochlorite tends to self-decompose during the reaction, but also organic compounds such as organic acids which are by-produced during the reaction consume sodium hypochlorite or accelerate the decomposition of sodium hypochlorite.

On the other hand, the oxidation reaction using an alkali hypohalite as an oxidizing agent is usually so exothermic that it is difficult to control the reaction with accuracy, resulting in the rise of the reaction temperature. The rise of the reaction temperature accelerates the reaction rate, which in turn causes a further rise of the reaction temperature. This is again a cause to increase the consumption of alkali hypohalite in the oxidation reaction.

The inventors have made an extensive study to solve the difficulties involved in the oxidation reaction wherein an alkali hypohalite is used as an oxidizing agent, and have found out that it is possible to control the reaction temperature accurately within optimum ranges of temperature by carrying out the oxidation reaction with concurrently distilling off a solvent used under a reduced pressure to reduce the amount of an alkali hypohalite consumed in the reaction.

An object of the invention is therefore to provide a method of performing an oxidation reaction using an alkali hypohalite as an oxidizing agent in an aqueous medium which is controllable in the reaction temperature within optimum ranges and reducible in the amount of alkali hypohalite consumed in the reaction.

A method of performing an oxidation reaction of the invention in which an alkali hypohalite is used as an oxidizing agent comprises: carrying out the oxidation reaction in an aqueous medium with concurrently distilling off an solvent used in the reaction as the reaction proceeds under a reduced pressure.

Any alkali hypohalite is usable in the invention provided that it is known as an oxidizing agent for organic compounds, and it includes sodium hypochlorite, potassium hypochlorite, sodium hypobromite, potassium hypobromite, calcium hypochlorite, etc. Among these hypohalites is most advantageously usable sodium hypochlorite since the hypohalite is the least expensive of the alkali hypohalites and most frequently used in oxidation reactions.

The method of the invention is applicable to any exothermic oxidation reaction in which an alkali hypohalite is used as an oxidizing agent to evolve a large amount of reaction heat. Specific examples of such oxidation reactions are an oxidation reaction of diacetone-L-sorbose to diacetone-2-keto-L-gulonic acid which is useful as a starting matetial for vitamin C as previously mentioned, an oxidation of furfural as dsecribed in Chemical Abstracts, Vol. 98, 98: 53578z, an oxidation of mesityl oxide as described in "Experimental Chemistry Course," Vol. 17, p. 222, Maruzen K.K. (1957), an oxidation of naphthalenes as dsecribed in Chemical Abstracts, Vol. 87, 87: 70732k, and an oxidation of sulfides as described in "Experimental Chemistry Course," Vol.17, p. 216, Maruzen K.K. (1957).

The method of the invention is in particular advantageously applicable to the oxidation of diacetone-L-sorbose to diacetone-2-keto-L-gulonic acid by sodium hypochlorite, and the invention will be fully set forth taking the reaction as an example.

In the oxidation reaction by sodium hypochlorite of diacetone-L-sorbose to diacetone-2-keto-L-gulonic acid, water is usually used as a solvent and inorganic nickel salts such as nickel halide, e.g., nickel chloride, and nickel sulfate as a catalyst. According to the conventional method, sodium hypochlorite is used in amounts of about 1.3 to 3 times the theoretical amount, as hereinbefore described, however, according to the invention, the amount of sodium hypochlorite consumed is less than the amount in the conventional oxidation reaction method by about 5–20%.

The method of the invention is applicable to any manner of reaction, namely, to either batchwise or semi-batchwise or continuous reactions.

In the oxidation reaction according to the invention, the pressure inside a reaction vessel is first reduced to about 90–350 Torr, preferably about 145–280 Torr so that the reaction mixture has a boiling point in the range of about 50°–80° C., preferably about 60°–75° C. Then, in a batchwise reaction, an aqueous solution of diacetone-L-sorbose and an aqueous solution of sodium hypochlorite of from room temperature to the reaction temperature are fed into the reaction vessel under the reduced pressure, and then an aqueous solution of nickel catalyst is fed into the reaction vessel to start the oxidation reaction. In a semi-batchwise or continuous reaction, an aqueous solution of diacetone-L-sorbose, an aqueous solution of sodium hypochlorite and an aqueous solution of nickel catalyst all of from room temperature to the reaction temperature are fed concurrently into the reaction vessel under the reduced pressure at a constant rate to initiate the oxidation reaction.

As soon as the oxidation reaction starts, the reaction temperature rises on account of reaction heat, and at last the water as a reaction solvent begins to boil, which is then continuously distilled off as the reaction proceeds. The amount and rate of distillation of water are dependent upon the amount and feeding rate of sodium hypochlorite, the amount of reactant used, and the manner in which the oxidation reaction is carried out, for example, however, it is usually preferred that an amount of about 1–2 kg of water is distilled off per kg of sodium hypochlorite used so as to accurately control the reaction temperature throughout the oxidation reaction. However, the amount of water distilled off is not critical in the invention. In the batchwise reaction, the reaction rate is large at an initial stage, and becomes smaller with time, so that the distilling rate of water is also large at an initial stage of the reaction, and becomes smaller with time as the reaction proceeds.

In the method of the invention, the reaction heat evolved is removed as latent heat of vaporization of water as water is distilled off as the reaction proceeds, so that the reaction temperature is controlled with accuracy, and the reaction temperature can be, for instance, controlled within ±1° C. of reaction temperature which has been predetermined. Therefore, the thermal decomposition of sodium hypochlorite is repressed to reduce the amount of sodium hypochlorite consumed in the reaction. Further, diacetone-2-keto-L-gulonic acid can be produced in the same yield as in the conventional method by the use of a lesser amount of sodium hypochlorite than in the conventional method.

As further advantages of the invention, by-produced organic acids, such as citric acid and oxalic acid, and decomposition products of discetone-L-sorbose, such as acetone and carbohydrates, are removed from the reaction mixture together with the solvent distilled off, to substantially reduce the amount of the sodium hypochlorite used in the oxidation reaction. These by-products and decomposition products otherwise consume certain amounts of sodium hypochlorite since they are also oxidized by the hypochlorite, or accelerate the self-decomposition of the hypochlorite, to increase the amount of sodium hypochlorite used in the oxidation reaction.

As a further aspect of the invention, the method of the invention is applicable to any manner of oxidation reaction of diacetone-L-sorbose, although the oxidation reaction has been hitherto limited in the reaction manner to a continuous reaction in which a reaction vessel is used which is provided with an efficient heat-removing device, as described in Japanese Published Unexamined Patent Application No. 37-1849, because the reaction is greatly exothermic. The reaction time is mainly dependent upon the reaction temperature. However, in the batchwise reaction, the distillation of water ceases usually in about 60–90 minutes and the reaction concludes after the start of the reaction. In the semi-batchwise reaction, the discontinuation of feeding of reactants causes the discontinuation of distillation of water, and after aging of the reaction mixture for about 30–60 minutes, the reaction is concluded. In the continuous reaction, the reaction time is dependent upon the number of reaction vessels as well as the reaction temperature, however, the residence time is usually about 2–4 hours.

The method of the invention is advantageous in that the amount of an alkali hypohalite used in the oxidation reaction is less than in the prior method, since the reaction temperature is copntrollable within optimum ranges with accuracy, thereby to prevent the undesired rise of reaction temperature and hence the self-decomposition of the alkali hypohalite used.

In the prior method, by-produced organic acides such as acetic acid or oxalic acid remain in the reaction mixture throughout the reaction, so that more or less amounts of alkali hypohalite are inevitably consumed for the oxidation of these by-products, which is a cause for the prior method to need to use a large amount of alkali hypohalite in the reaction. According to the invention on the contrary to the above, since the by-produced organic compounds, volatile components, as above are removed from the reaction mixture together with the solvent as the reaction proceeds, the amount of alkali hypohalite needed is substantially reduced.

Further the reaction heat evolved in the oxidation reaction is removed efficiently in the method of the invention, the oxidation reaction may be carried out even by the use of a reaction vessel provided with no heat-removing device such as coils or jackets. Namely, the method of the invention needs a lesser amount of energy for removing the reaction heat. Meanwhile, the oxidation reaction by an alkali hypohalite has hitherto been carried out dividedly by the use of a plurality of reaction vessels to disperse the reaction heat evolved, however, the method of the invention is applicable to any manner of reaction, so that the expenditures for installments are less than in the conventional method of reaction.

The invention will be understood more readily with reference to the following examples; however, these examples are intended to illustrate the invention only and are not to be construed as limitation to the invention.

EXAMPLE 1

An amount of 300 g of a 33.3% by weight of an aqueous solution of diacetone-L-sorbose and 6 ml of a 5% by weight of an aqueous solution of nickel chloride as a catalyst both of which had been in advance heated to 70° C. were fed into an 1 l-capacity reaction vessel kep under a reduced pressure of 300 Torr, and then a 12.5% by weight aqueous solution of sodium hypochlorite was added in a time to the solution in molar ratios as shown in Table 1, thereby to start the reaction.

The reaction mixture began to boil at a temperature of 75° C., and an amount of about 100 ml of water was distilled off as the reaction proceeds in 60 minutes, to conclude the reaction. The resultant reaction mixture was filtered to remove the catalyst, and cooled to 5° C., and then a 35% hydrochloric acid was added to the mixture to put it at a pH of 1.5, to crystallize out diacetone-2-keto-L-gulonic acid.

For a comparison, the same reaction vessel as above the inside of which was under atmospheric pressure was placed in water at 75° C., and the aqueous solutions of diacetone-L-sorbose, nickel chloride and sodium hypochlorite were fed into the reaction vessel in the same manner as above. The reaction temperature was found to rise temporarily to 85°–90° C., and then lowered to 75° C. The reaction concluded in 60 minutes. The resultant reaction mixture was worked up in the same manner as above, to provide diacetone-2-keto-L-gulonic acid.

The amount of solution of sodium hypochlorite used and the yield of resultant diacetone-2-keto-L-gulonic acid are shown in Table 1.

TABLE 1

| Amount of Sodium Chlorite | | Yield[1] | |
|---|---|---|---|
| Amount of Solution (ml) | Molar Ratios[2] | Example (g) | Comparison (g) |
| 453 | 2.40 | 105.2 | 98.7 |
| 510 | 2.70 | 105.0 | 103.5 |
| 567 | 3.00 | 105.3 | 105.2 |

[1]Of diacetone-2-keto-L-gulonic acid.
[2]To diacetone-L-sorbose.

As apparent from the above result, the amount of sodium hypochlorite necessary to obtain a maximum yield of discetone-2-keto-L-gulonic acid is reduced by as much as about 20% than in the conventional manner of reaction.

EXAMPLE 2

Two 500 ml-capacity reaction vessels were kept at a reduced pressure of 240 Torr. To the first reaction vessel were fed a 33.3% by weight of an aqueous solution of diacetone-L-sorbose at a rate of 150 g/hour, and a 5% by weight of an aqueous solution of nickel chloride at a rate of 3 ml/hour, and a 12.5% by weight aqueous solution of sodium hypochlorite at a rate as shown in Table 2, with a constant volume pump. The reaction mixture boiled at a temperature of 70° C. After 6 hours from the start of feeding of the reactants, the effluent from the second reaction vessel was sampled for 1 hour, and was worked up in the same manner as in Example 1, to provide diacetone-2-keto-L-gulonic acid.

For a comparison, the same reaction vessels as above were placed on a water bath at 70° C., and the aqueous solutions of diacetone-L-sorbose, nickel chloride and sodium hypochlorite were fed into the first reaction vessel in the same manner as above, to start the reaction under atmospheric pressure. The reaction temperature was found to temporarily rise to 70°–75° C. After 6 hour, the effluent from the second reaction vessel was sampled for 1 hours, and was worked up in the same manner as in Example 1, to provide diacetone-2-keto-L-gulonic acid.

The amount of solution of sodium hypochlorite used and the yield of resultant diacetone-2-keto-L-gulonic acid are shown in Table 2.

TABLE 2

| Amount of Sodium Chlorite | | Yield[1] | |
|---|---|---|---|
| Amount of Solution (ml/hr.) | Molar Ratios[2] | Example (g) | Comparison (g) |
| 227 | 2.40 | 52.5 | 49.6 |
| 255 | 2.70 | 52.7 | 52.0 |
| 283 | 3.00 | 52.6 | 52.6 |

[1]Of diacetone-2-keto-L-gulonic acid.
[2]To diacetone-L-sorbose.

As apparent from the above result, the amount of sodium hypochlorite necessary to obtain a maximum yield of diacetone-2-keto-L-gulonic acid is less than in the conventional manner of reaction.

EXAMPLE 3

To an 150 l-capacity reaction vessel kept at a reduced pressure of 300 Torr were fed 450 kg of a 33.3% by weight of an aqueous solution of diacetone-L-sorbose, 9 l of a 5% by weight of an aqueous solution of nickel chloride and a 12.5% by weight aqueous solution of sodium hypochlorite in amounts shown in Table 3 concurrently with each other in 1 hour. The reaction started at once, and boiled at 75° C. An amount of about 160 l of water was distilled off as the reaction proceeds, when the reaction concluded. The reaction mixture was worked up in the same manner as in Example 1, to provide diacetone-2-keto-L-gulonic acid.

For a comparison, the same reaction vessel as above was placed in water, and the aqueous solutions of diacetone-L-sorbose, nickel chloride and sodium hypochlorite were fed into the reaction vessel in the same manner as above. The reaction was, however, carried out under normal pressure. The reaction temperature was found to vary in the range of from 60° C. to 88° C.

The amount of solution of sodium hypochlorite used and the yield of resultant diacetone-2-keto-L-gulonic acid are shown in Table 3.

TABLE 3

| Amount of Sodium Chlorite | | Yield[1] | |
|---|---|---|---|
| Amount of Solution (ml) | Molar Ratios[2] | Example (g) | Comparison (g) |
| 680 | 2.40 | 158.2 | 146.3 |
| 765 | 2.70 | 157.7 | 155.7 |
| 851 | 3.00 | 158.4 | 158.2 |

[1]Of diacetone-2-keto-L-gulonic acid.
[2]To diacetone-L-sorbose.

As apparent from the above result, the amount of sodium hypochlorite necessary to obtain a maximum yield of diacetone-2-keto-L-gulonic acid is less than in the conventional manner of reaction.

What is claimed is:

1. A method of performing an oxidation reaction in which an alkali hypohalite is used as an oxidizing agent which comprises: carrying out the oxidation reaction in an aqueous medium with concurrently distilling off a solvent used in the reaction as the reaction proceeds under a reduced pressure.

2. The method of performing an oxidation reaction as claimed in claim 1 wherein the alkali hypohalite is sodium hypochlorite.

3. The method of performing an oxidation reaction as claimed in claim 1 wherein the oxidation reaction is a reaction of diacetone-L-sorbose to diacetone-2-keto-L-gulonic acid.

4. The method of performing an oxidation reaction as claimed in claim 3 wherein the alkali hypohalite is sodium hypochlorite.

5. The method of performing an oxidation reaction as claimed in claim 3 wherein the reaction is carried out under a reduced pressure of about 90–350 Torr so that the reaction mixture has a boiling point in the range of about 50°–80° C.

* * * * *